United States Patent
Yamamoto et al.

(10) Patent No.: US 11,926,991 B2
(45) Date of Patent: Mar. 12, 2024

(54) SENSIBILITY FEEDBACK CONTROL DEVICE

(71) Applicants: KOBELCO CONSTRUCTION MACHINERY CO., LTD., Hiroshima (JP); HIROSHIMA UNIVERSITY, Higashi-Hiroshima (JP)

(72) Inventors: Toru Yamamoto, Hiroshima (JP); Takuya Kinoshita, Hiroshima (JP)

(73) Assignees: KOBELCO CONSTRUCTION MACHINERY CO., LTD., Hiroshima (JP); HIROSHIMA UNIVERSITY, Higashi-Hiroshima (JP)

( * ) Notice: Subject to any disclaimer, the term of this patent is extended or adjusted under 35 U.S.C. 154(b) by 380 days.

(21) Appl. No.: 17/288,757

(22) PCT Filed: Oct. 25, 2019

(86) PCT No.: PCT/JP2019/041919
§ 371 (c)(1),
(2) Date: Apr. 26, 2021

(87) PCT Pub. No.: WO2020/090659
PCT Pub. Date: May 7, 2020

(65) Prior Publication Data
US 2021/0395977 A1 Dec. 23, 2021

(30) Foreign Application Priority Data
Nov. 1, 2018 (JP) .................................. 2018-206633

(51) Int. Cl.
*E02F 9/20* (2006.01)
*B60R 16/037* (2006.01)
*G05B 6/02* (2006.01)

(52) U.S. Cl.
CPC .......... *E02F 9/2025* (2013.01); *B60R 16/037* (2013.01); *G05B 6/02* (2013.01); *E02F 9/2004* (2013.01)

(58) Field of Classification Search
None
See application file for complete search history.

(56) References Cited

U.S. PATENT DOCUMENTS 9,988,791 B2 * 6/2018 Uji ...................... B60R 16/0234
2018/0031405 A1 2/2018 Berentsen et al.
(Continued)

FOREIGN PATENT DOCUMENTS

JP  2012-22041 A  2/2012
JP  2017-74356 A  4/2017
(Continued)

OTHER PUBLICATIONS

International Search Report dated Dec. 24, 2019 in PCT/JP2019/041919 filed Oct. 25, 2019, 2 pages.
(Continued)

*Primary Examiner* — Todd Melton
(74) *Attorney, Agent, or Firm* — Oblon, McClelland, Maier & Neustadt, L.L.P.

(57) ABSTRACT

A sensibility meter detects biometric information relating to an operator corresponding to an output from a target appliance, and determines a comfort level of the operator based on the biometric information. A first control unit determines a second target value relating to the output based on a difference between a first target value relating to the comfort level and the comfort level. A second control unit determines a control input to the target appliance based on a difference between the second target value and the output. A δ setting unit performs weighting corresponding to an operation level of the operator, for an operation input to the target appliance (Continued)

by the operator, and for the control input. An adder adds the weighted operation input and control input, and inputs the resultant to the target appliance.

6 Claims, 11 Drawing Sheets

(56) References Cited

U.S. PATENT DOCUMENTS

| | | | |
|---|---|---|---|
| 2018/0055403 | A1 | 3/2018 | Yamamoto et al. |
| 2018/0303370 | A1 | 10/2018 | Kanayama et al. |

FOREIGN PATENT DOCUMENTS

| | | |
|---|---|---|
| JP | 2017-136922 A | 8/2017 |
| JP | 2018-36773 A | 3/2018 |
| WO | WO 2013/006639 A1 | 1/2013 |
| WO | WO 2017/104793 A1 | 6/2017 |

OTHER PUBLICATIONS

Wakitani, S., et al., "Design of Nonlinear PID Control System by use of FRIT method", Journal of the Society of Instrument and Control Engineers, vol. 52, No. 10, 2013, pp. 885-891, 10 total pages (with Partial English Translation).

Ziegler, J.G., et al., "Optimum Settings for Automatic Controllers", Transactions of the A.S.M.E., vol. 64, No. 8, 1942, pp. 759-768.

Chien, K. L., et al., "On the Automatic Control of Generalized Passive Systems", Transactions of the A.S.M.E., vol. 74, 1972, pp. 175-185.

Herman, I.P., "Physics of the Human Body: Biological and Medical Physics", Second Edition, Biomedical Engineering, Springer-Verlag GmbH & Co. KG, 2007, 12 total pages.

Van Der Helm, P.A., "Weber-Fechner behavior in symmetry perception?", Attention, Perception, & Psychophysics, vol. 72, No. 7, 2010, pp. 1854-1864.

Extended European Search Report dated Nov. 12, 2021 in European Patent Application No. 19879978.5, 5 pages.

\* cited by examiner

FIG. 8
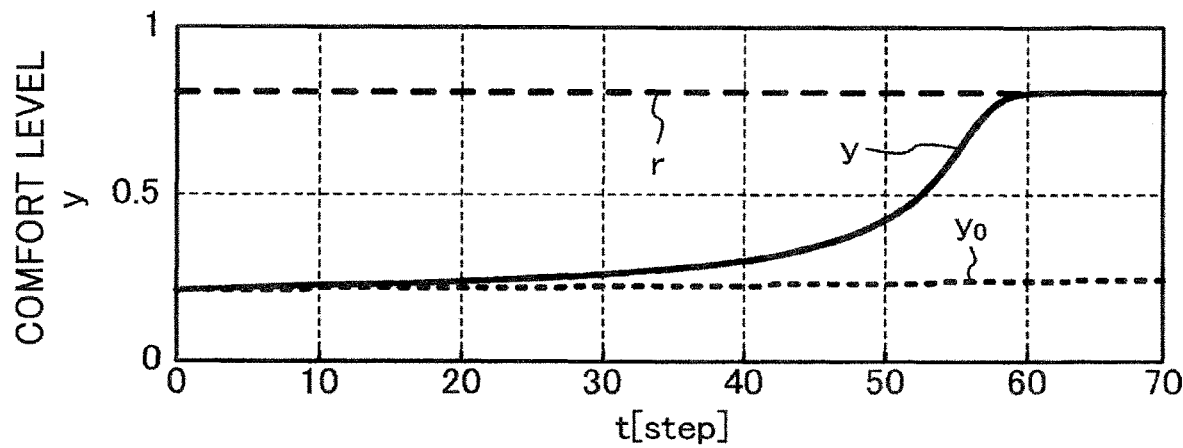
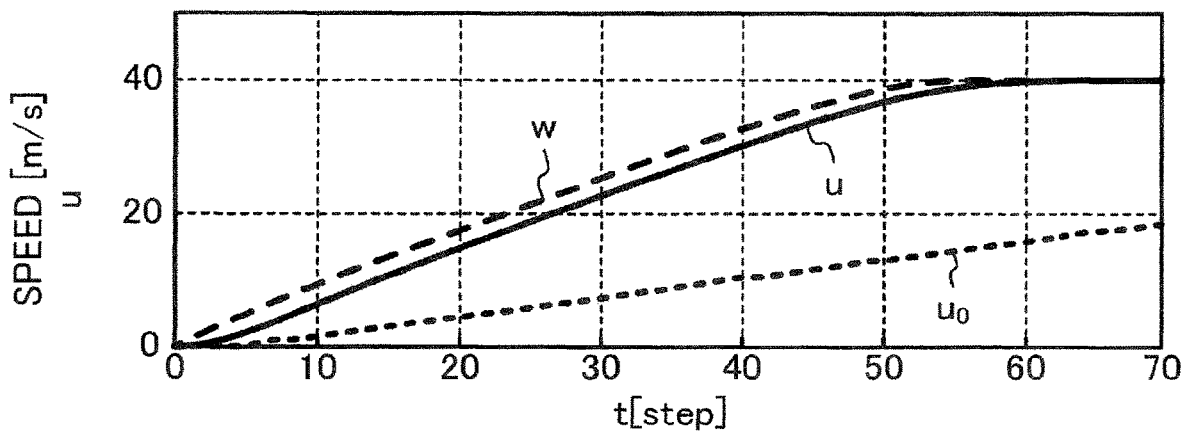
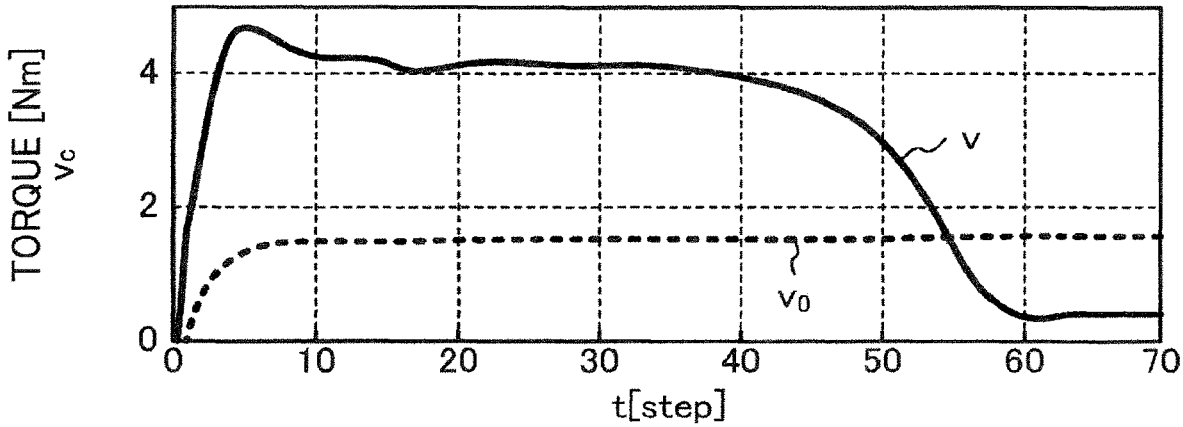

FIG. 9
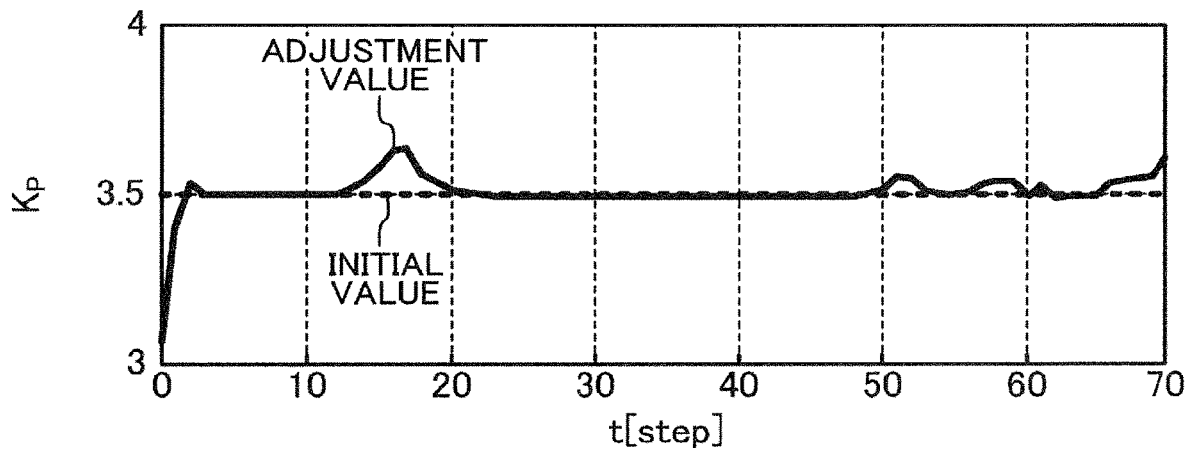
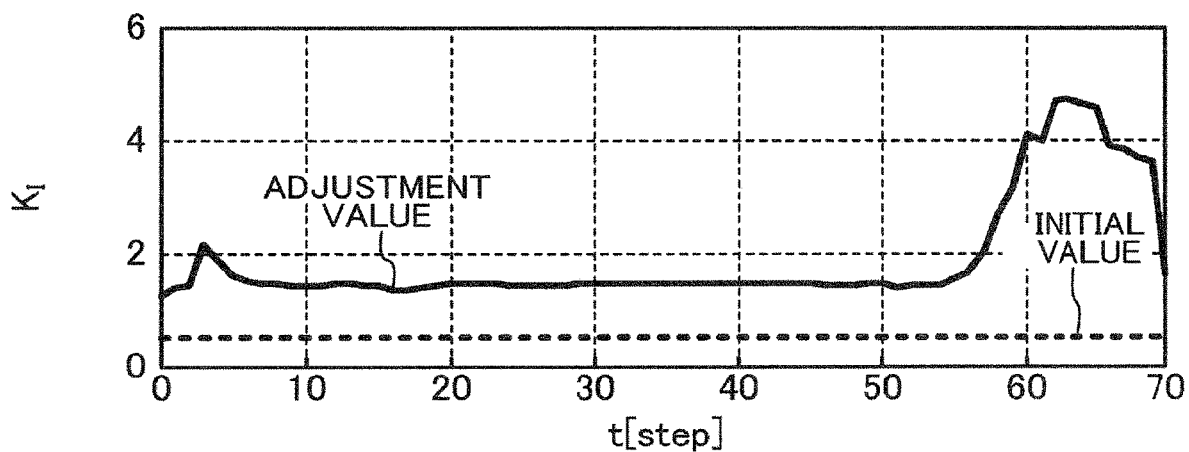
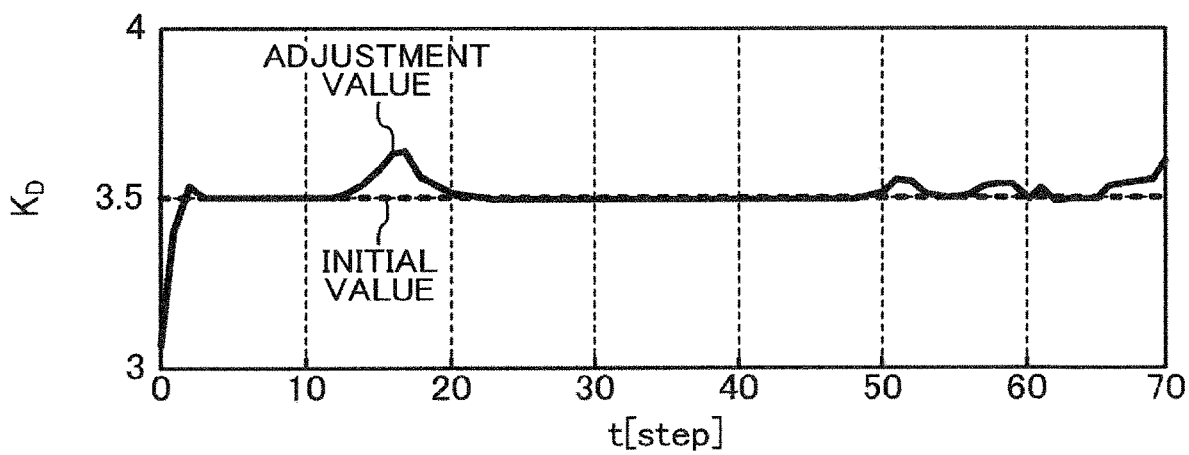

FIG. 11
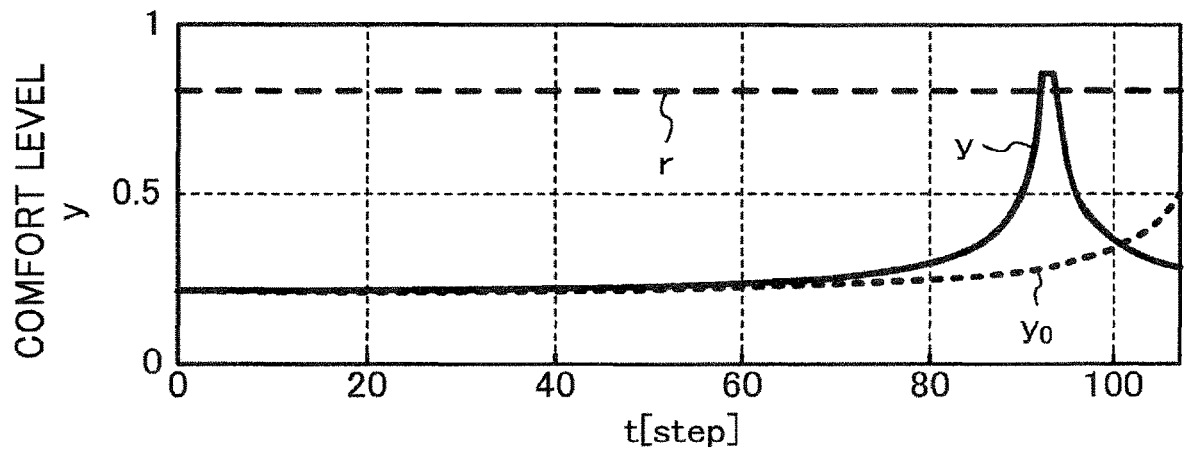
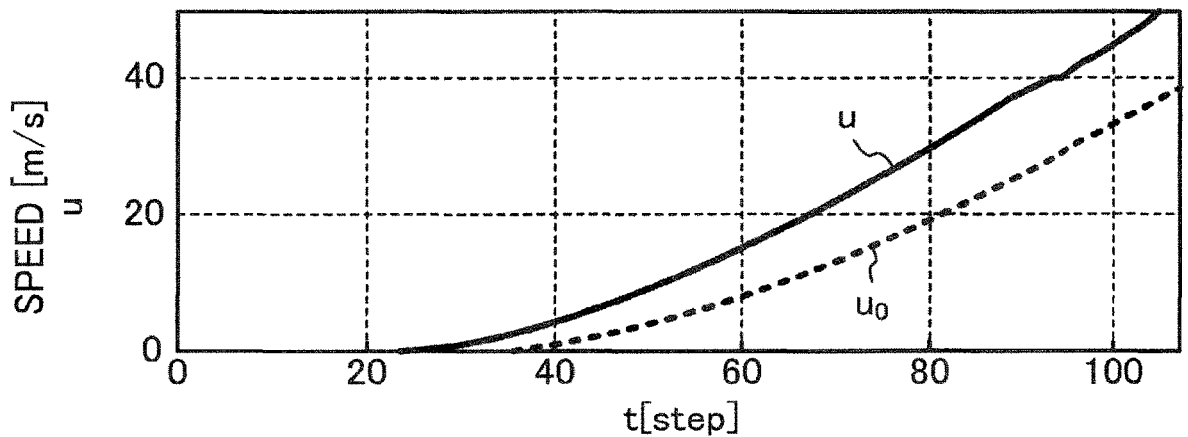
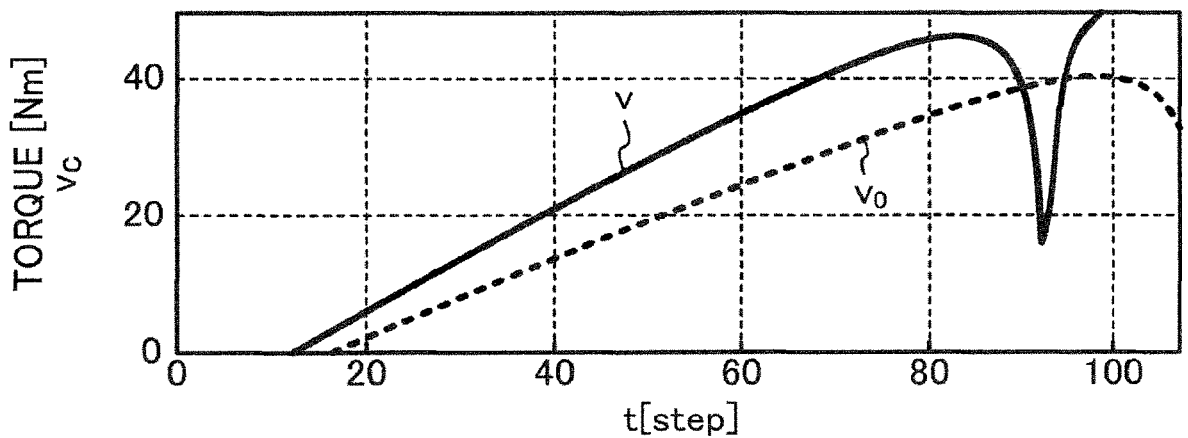

SENSIBILITY FEEDBACK CONTROL DEVICE

TECHNICAL FIELD

The present invention relates to a sensibility feedback control device.

BACKGROUND ART

A survey by the Cabinet Office, Government of Japan indicates that Japan has a low level of happiness in spite of its high gross domestic product (GDP). That is, there is a large gap between "material richness" relevant to GDP and "mental richness" relevant to the level of happiness.

As one of the measures to fill this gap, it is considered to improve mental richness by already advanced "material" (such as welfare support appliance) performing actions in consideration of human sensibility (e.g., Patent Literature 1). Researches on the visualization technology of "sensibility" have been conducted assuming social implementation (e.g., Patent Literature 2).

However, most of the researches on sensibility deal with static fields such as product design evaluation and design. Few researches have been conducted on dynamic control of the sensibility of the operator especially for the appliance such as automobiles and construction machines operated by the operator.

CITATION LIST

Patent Literature

Patent Literature 1: JP 2018-36773 A
Patent Literature 2: JP 2017-74356 A

SUMMARY OF INVENTION

Therefore, an object of the present invention is to provide a sensibility feedback control device capable of feedback controlling the sensibility of an operator in an appliance operated by the operator.

A sensibility feedback device according to one aspect of the present invention includes: a target appliance to be operated by an operator; a sensibility meter that detects biometric information x(t) relating to the operator corresponding to an output u(t) from the target appliance, and determines a comfort level y(t) of the operator based on the biometric information x(t); a first control unit that determines a second target value w(t) relating to the output u(t) based on a difference between a first target value r(t) relating to the comfort level y(t) and the comfort level y(t); a second control unit that determines a control input $v_c(t)$ to the target appliance based on a difference between the second target value w(t) and the output u(t); a weight setting unit that performs weighting corresponding to an operation level of the operator, for an operation input $v_h(t)$ to the target appliance by the operator, and for the control input $v_c(t)$; and an adder that adds the operation input $v_h(t)$ and the control input $v_c(t)$, each of which has been weighted by the weight setting unit, and inputs an added value to the target appliance.

BRIEF DESCRIPTION OF DRAWINGS

FIG. 8 shows graphs showing the comfort level y(t), an output u(t) (speed), and a control input v(t) (torque) in each step (time) in the present numerical example.

FIG. 9 shows graphs showing adjusted control parameters (PID gain) at each step (time).

FIG. 11 shows graphs showing a result of performing sensibility feedback control while performing adjustment of a control parameter of a control unit by database-driven control in the comparative example.

DESCRIPTION OF EMBODIMENTS

The sensibility feedback control device according to an embodiment of the present invention will be described below with reference to the drawings. Note that the scope of the present invention is not limited to the following embodiments, and can be optionally changed within the scope of the technical idea of the present invention.

Figure 1:
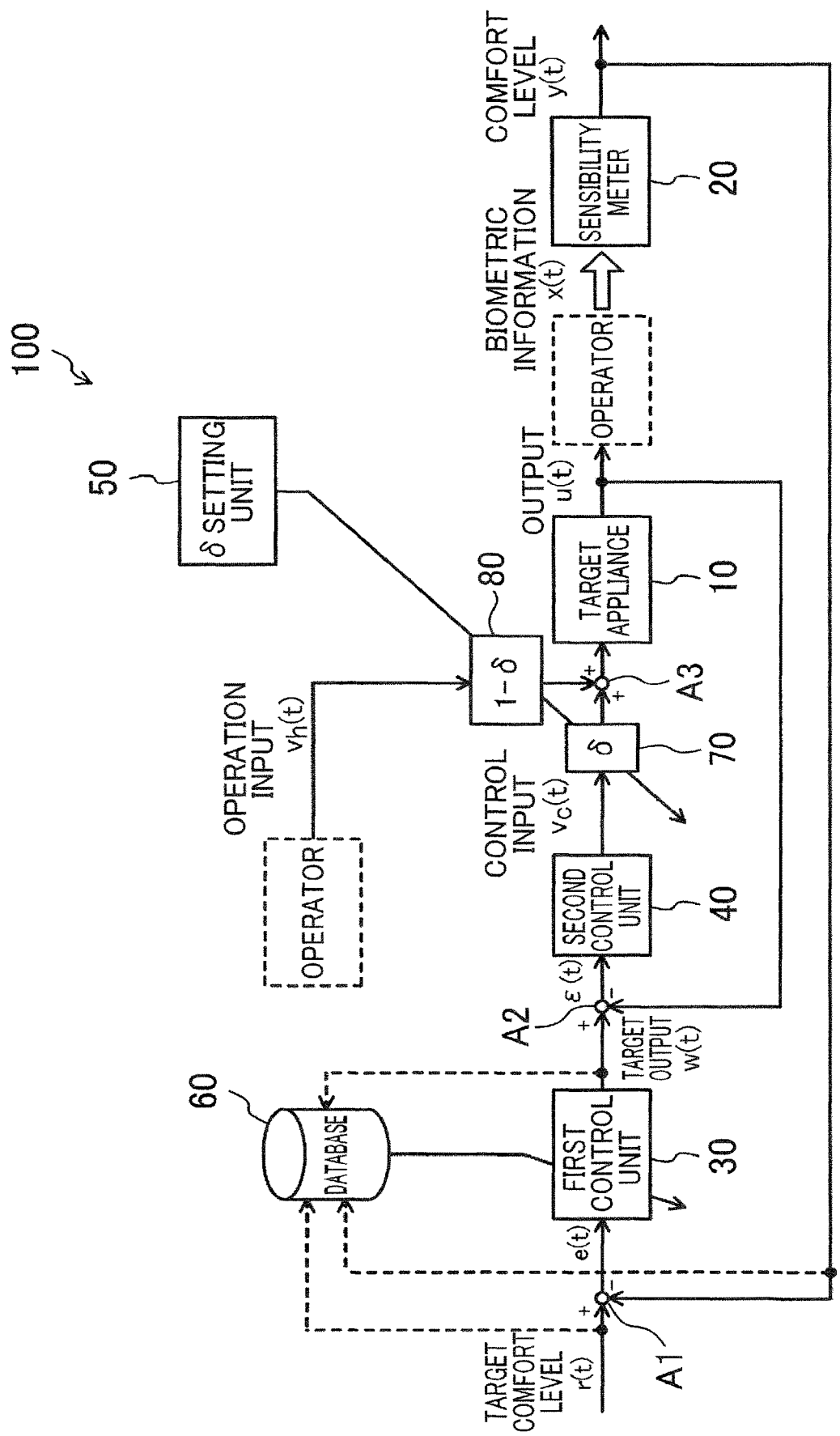
FIG. 1 is a configuration diagram of a sensibility feedback control device according to an embodiment.

FIG. 1 is a configuration diagram of the sensibility feedback control device according to the embodiment. As shown in FIG. 1, a sensibility feedback control device 100 includes a target appliance 10, a sensibility meter 20, a first control unit 30, a second control unit 40, a 6 setting unit 50, a database 60, a control input adjustment unit 70, and an operation input adjustment unit 80. The δ setting unit 50, the control input adjustment unit 70, and the operation input adjustment unit 80 are examples of a weight setting unit. Furthermore, the sensibility feedback control device 100 includes subtractors A1 and A2 and an adder A3. The target appliance 10 is an appliance to be operated by an operator, for example, an automobile or a construction machine. In FIG. 1, the first control unit 30, the second control unit 40, the sensibility meter 20, the subtractors A1 and A2, and the adder A3 are configured with a processor such as a CPU. The database 60 is configured with a non-volatile memory such as a solid-state drive or hard disk drive.

The sensibility meter 20 detects biometric information x(t) relating to the operator corresponding to an output u(t) from the target appliance 10, and determines a comfort level y(t) of the operator based on the biometric information x(t). The output u(t) of the target appliance 10 is, for example, the response speed of a hydraulic excavator.

The subtractor A1 calculates a difference e(t) between a first target value (target comfort level r(t)) and the comfort level y(t), and inputs the difference e(t) to the first control unit 30.

Based on the difference e(t) calculated by the subtractor A1, the first control unit 30 determines a second target value (target output w(t)) related to the output u(t) and inputs the second target value to the subtractor A2.

The subtractor A2 calculates a difference ε(t) between the target output w(t) and the output u(t), and inputs the difference ε(t) to the second control unit 40.

Based on the difference ε(t) calculated by the subtractor A2, the second control unit 40 determines a control input $v_c(t)$ to the target appliance 10, and inputs the control input $v_c(t)$ to the control input adjustment unit 70.

The δ setting unit 50 sets a weight value (1−δ) with respect to the operation input $v_h(t)$ to the target appliance 10 by the operator. The δ setting unit 50 sets a weight value (δ) with respect to the control input $v_c(t)$. The δ setting unit 50 sets the weight value (1−δ) and the weight value (δ) in accordance with the operation level of the operator.

The control input adjustment unit 70 multiplies the control input $v_c(t)$ by the weight value (δ) with respect to the control input $v_c(t)$ set by the δ setting unit 50, and inputs the resultant to the adder A3.

The operation input adjustment unit 80 multiplies the operation input $v_h(t)$ by the weight value (1−δ) with respect to the operation input $v_h(t)$ set by the δ setting unit 50, and inputs the resultant to the adder A3.

The adder A3 adds $\delta \cdot v_c(t)$ having been input from the control input adjustment unit 70 and $(1-\delta) \cdot v_h(t)$ having been input from the operation input adjustment unit 80, and inputs the added value to the target appliance 10.

The target appliance 10 acquires the added value having been input from the adder A3, and calculates the output u(t) in accordance with the added value.

Next, the sensibility meter 20 will be described in detail.

(Sensibility Meter)

In the present embodiment, the sensibility meter 20 calculates the comfort level y(t) based on the biometric information x(t) of the operator corresponding to the output u(t) of the target appliance. The biometric information x(t) of the operator includes, for example, the facial expression of the operator, the skin resistance of the operator, the upper limb myoelectricity of the operator, the lower limb myoelectricity of the operator, and voice information presenting the voice of the operator. The sensibility meter 20 is only required to detect the facial expression of the operator by a CCD camera, for example. The sensibility meter 20 is only required to detect the heartbeat by a heartbeat sensor, for example. The sensibility meter 20 is only required to detect respiration (number of times and depth) by a CCD camera, for example. The sensibility meter 20 is only required to detect skin resistance by a skin impedance sensor. The sensibility meter 20 is only required to detect upper limb myoelectricity and lower limb myoelectricity by a myoelectric sensor, for example. The sensibility meter 20 is only required to detect voice information by a microphone.

When a human sees, hears, touches, or is touched by something, he or she sometimes has a feeling or emotion such as throbbing, getting excited, getting exhilarated, or getting thrilled. Such feelings or emotions are brought about by a complex, higher brain activity of the human. Formation of feelings or emotions is deeply involved with the somatic nervous system including motor nerve and sensory nerve, and the autonomic nervous system including sympathetic nerve and parasympathetic nerve, as well as memories or experiences. Hence, sensibility is defined as a higher brain function that takes a higher-level overview of emotional responses, which are caused by comparing information in which exteroceptive sensory information (somatic nervous system information) and interoceptive sensory information (autonomic nervous system information) are integrated with past experiences and memories. In other words, the sensibility is a higher brain function that causes a human to recognize a gap between prediction (image) and outcome (sensory information) as "aha!" by comparing the gap with experiences and knowledge.

The sensibility, which is such a higher brain function, needs to be comprehensively understood from various viewpoints. The sensibility can be understood from the viewpoint of "comfort/discomfort" such as whether a human feels agreeable, comfortable, or pleasant, or on the contrary, whether a human feels disagreeable, uncomfortable, or unpleasant. Furthermore, the sensibility can be understood from the viewpoint of "active/inactive" such as whether a human is in an aroused, excited, or active state, or on the contrary, whether a human is in a vacant, calming, or inactive state. In addition, the sensibility can be understood from the viewpoint of "sense of anticipation" such as whether a human is excited to anticipate or expect something, or on the contrary, whether the excitement is hindered.

Russell's circumplex model, in which comfort/discomfort and active/inactive are expressed on two axes, is known. Feelings can be expressed by this circumplex model. However, the sensitivity is a higher brain function that compares the gap between prediction (image) and outcome (sensory information) with experiences and knowledge. Therefore, the sensibility cannot be fully expressed by the existing circumplex model made up of the two axes of comfort/discomfort and active/inactive. Therefore, in the present embodiment, the sensibility is captured by, for example, a sensibility multi-axis model in which a time axis (e.g., sense of anticipation) is added as the third axis to Russell's circumplex model.

Figure 2:
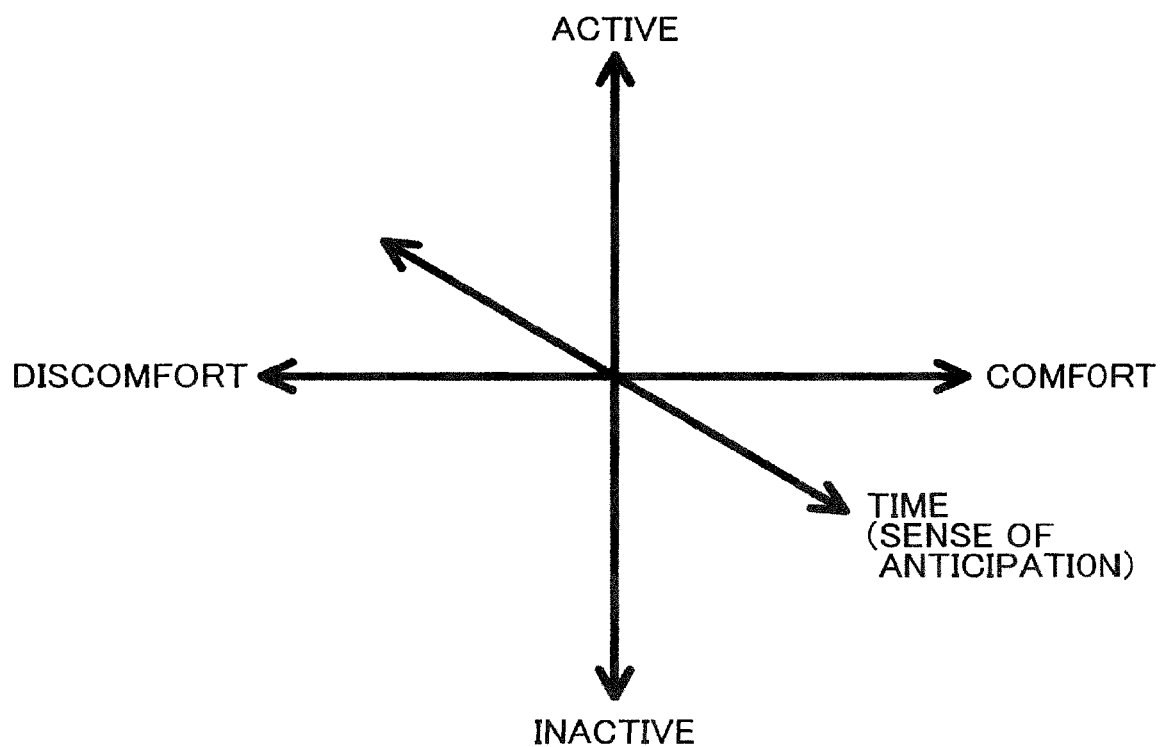
FIG. 2 is a schematic view of a sensibility multi-axis model used in the sensibility feedback control device according to the embodiment.

FIG. 2 is a schematic view of the sensibility multi-axis model used in the sensibility feedback control device according to the embodiment. As shown in FIG. 2, the sensibility multi-axis model can express "comfort/discomfort" (valence) as the first axis, "active/inactive" (arousal) as the second axis, and "time (sense of anticipation)" as the third axis. The advantage of multi-axis modeling of sensibility lies in that calculating and integrating the evaluation value of each axis enable the quantitative evaluation, i.e., visualization of the sensibility, which has a vague, wide concept. Specifically, the brain physiological index value (EEG comfort, EEG active, and EEG sense of anticipation) of each axis is obtained from the brain physiological information of each axis of the sensibility multi-axis model. From subjective statistical data of the subject, a subjective psychological axis showing weighting coefficients (a, b, c) of each axis of the sensibility multi-axis model is obtained. Then, the sensibility value can be evaluated by the following calculation expression using the brain physiological index value and the subjective psychological axis. The subjective statistical data of the subject is data indicating the relationship between the brain wave of the subject in a certain state and the response (subjectivity) of the subject to the state, and is data learned in advance.

Sensibility value=[Subjective psychological axis]* [Brain physiological index value]=$a$*EEG comfort+$b$*EEG active+$c$*EEG sense of anticipation The sensibility meter 20 calculates the brain physiological index value by inputting biometric information x(t) detected by the above-mentioned various sensors, for example, into a predetermined calculation expression. Then, the sensibility meter 20 calculates the sensibility value by inputting the calculated brain physiological index value into the calculation expression. Then, the sensibility meter 20 outputs the calculated sensibility value as the comfort level y(t).

Next, the details of the first control unit 30 will be described.

(First Control Unit)

The first control unit 30 executes PID control represented by the following expression (1) using, for example, $K_P$, $K_I$, and $K_D$ as control parameters.

[Expression 1]

$$w(t) = K_P e(t) + K_I \int_0^t e(\tau) d\tau + K_D \frac{de(t)}{dt} \quad (1)$$

The target output w(t) is an operation amount in PID control. $K_P$, $K_I$, and $K_D$ are proportional gain, integral gain, and differential gain in PID control, respectively. The proportional gain, the integral gain, and the differential gain are referred to as PID gain. The difference e(t) is a deviation in PID control. Here, w(t) is adjusted so that the difference e(t) approaches zero.

In the present embodiment, an object is to improve the comfort level y(t) by bringing the comfort level y(t) closer to the target comfort level r(t), but it is difficult to set the target output w(t) suitable for each operator in feedback control. Therefore, the present embodiment employs a cascade control system as shown in FIG. 1. Thus, in the present embodiment, by giving the target comfort level r(t), it is possible to automatically generate the target output w(t) suitable for each operator. At this time, human sensibility is considered to be a time-varying system and a nonlinear system. Therefore, as shown in FIG. 1, the first control unit 30 performs feedback control using the database 60 (database-driven control: See, "Wakitani Shin, et al., Design of FRIT-Based Nonlinear PID Control Systems, Journal of the Society of Instrument and Control Engineers, Vol. 52, No. 10, pp. 885-891 (2013)", for example). In the database 60, data necessary for adjustment of the PID gain of the first control unit 30, for example, the target comfort level r(t), the comfort level y(t), the target output w(t), and the like are sequentially accumulated. For example, a predetermined value is adopted as the target comfort level r(t).

Figure 3:
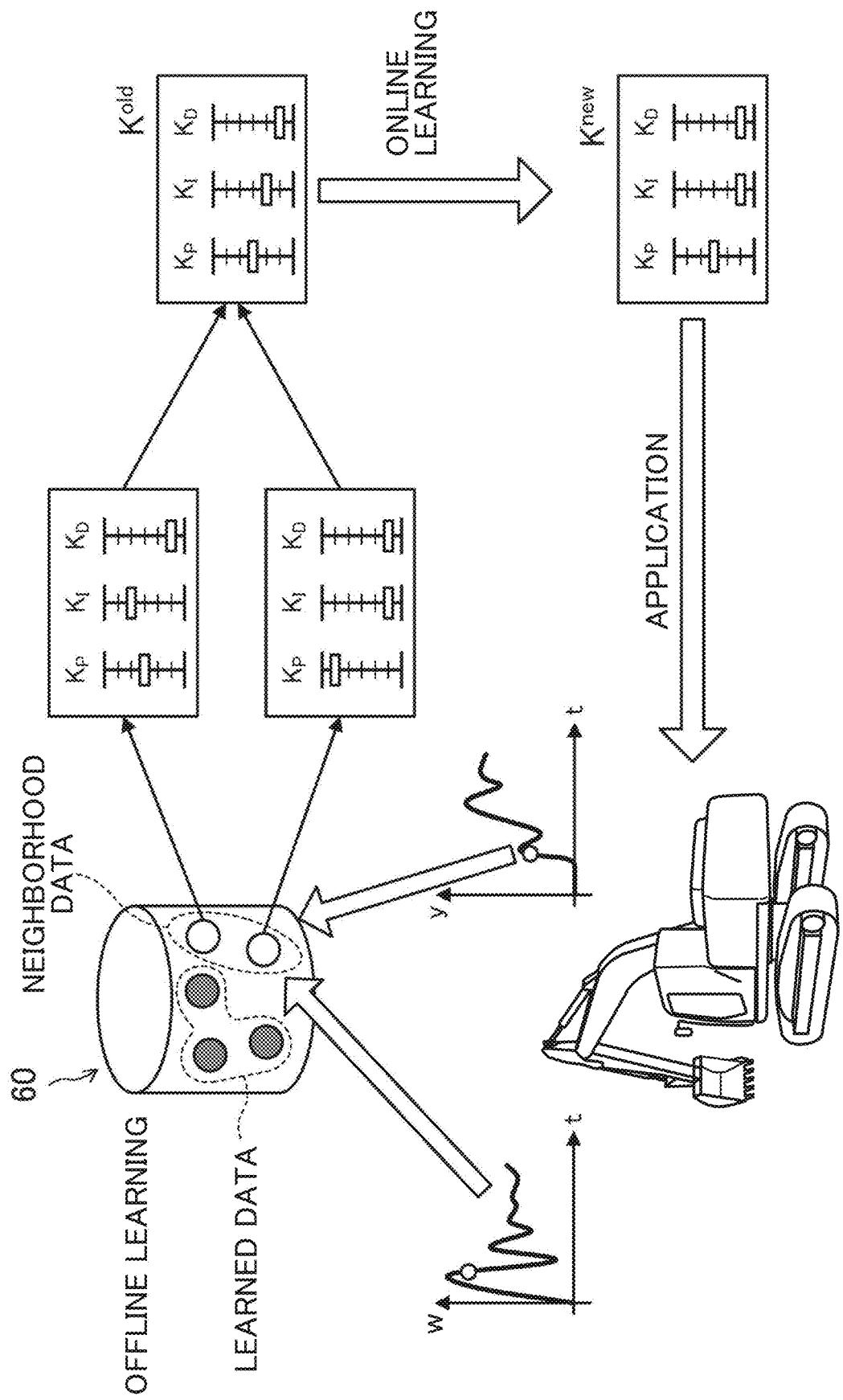
FIG. 3 is a view for explaining a database-driven control used in the sensibility feedback control device according to the embodiment.

FIG. 3 is a view for explaining the database-driven control used in the sensibility feedback control device according to the embodiment. The database-driven control of the first control unit 30 will be described in detail in the following examples. The database-driven control according to the present embodiment may use, for example, a learning function using the gradient method, or may use offline learning in which the gradient method and the fictitious reference iterative tuning (FRIT) method are combined or online learning in which the gradient method and the FRIT method are combined.

For example, in the present embodiment, the control parameter represented by the expression (1) is calculated based on the neighborhood data in the vicinity of the current state of the system among the data stored in the database 60. The control parameters calculated here are the control parameters obtained by the online learning described in the examples described later. However, this is one example, and the control parameter shown in the expression (1) may be a control parameter obtained by offline learning described in the examples described later.

Next, the details of the second control unit 40 will be described.

(Second Control Unit)

The second control unit 40 executes PID control represented by the following expression (2) using, for example, $K_P'$, $K_I'$, and $K_D'$ as control parameters.

[Expression 2]

$$v_c(t) = K_P' \varepsilon(t) + K_I' \int_0^t \varepsilon(\tau) d\tau + K_D' \frac{d\varepsilon(t)}{dt} \quad (2)$$

The control input $v_c(t)$ is an operation amount in PID control. $K_P'$, $K_I'$, and $K_D'$ are proportional gain, integral gain, and differential gain in PID control, respectively. The difference ε(t) is a deviation in PID control. Here, the control input $v_c(t)$ is adjusted so that the difference ε(t) becomes zero.

The control parameters of the second control unit 40 are, for example, existing parameters corresponding to the target appliance 10. The existing parameters may be fixed constants or may be variable parameters.

(δ Setting Unit)

The δ setting unit 50 basically sets a relatively low weight value (δ) for an operator with high skill, and sets a relatively high weight value (δ) for an operator with low skill. The δ setting unit 50 holds, for example, skill data in which the skill level of the operator evaluated in advance in five stages and a weight value (δ) corresponding to each skill level are associated. Then, when the skill level of the operator is input, the δ setting unit 50 is only required to determine, from the skill data, the weight value (δ) corresponding to the input skill level. Alternatively, the δ setting unit 50 may evaluate the level of the operator based on the test result when the operator performs the test operation, and may set the weight value (δ) based on the evaluation result.

(Effects)

As described above, in the sensibility feedback control device 100 of the present embodiment, the sensibility meter 20 detects the biometric information x(t) of the operator corresponding to the output u(t) of the target appliance 10, and determines the comfort level y(t) of the operator based on the biometric information x(t). The first control unit 30 determines the target output w(t) relating to the output u(t) based on the difference e(t) between the first target value (target comfort level) r(t) relating to the comfort level y(t) and the comfort level y(t). The second control unit 40 determines the control input $v_c(t)$ to the target appliance 10 based on the difference ε(t) between the target output w(t) and the output u(t). Thus, the sensibility feedback control device 100 can perform control in which the sensibility (specifically, comfort level y(t)) of the operator to the target appliance 10 is fed back by using the sensibility meter 20, the first control unit 30, and the second control unit 40.

Figure 4:
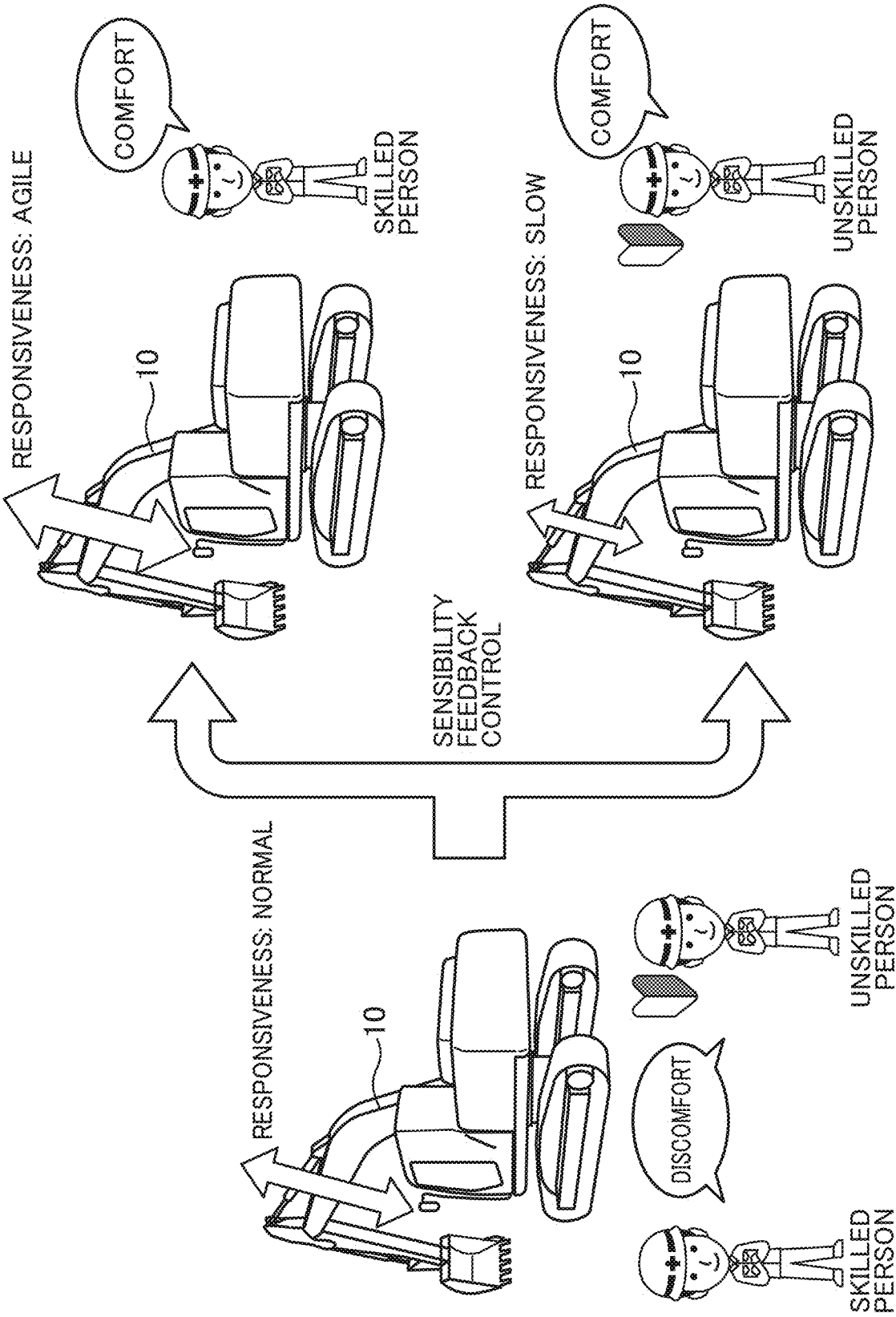
FIG. 4 is a view showing an effect obtained by the sensibility feedback control device according to the embodiment.

FIG. 4 is a view showing the effect obtained by the sensibility feedback control device 100 of the present embodiment. In the example of FIG. 4, the sensibility feedback control device 100 is applied to the target appliance 10 made up of a hydraulic excavator, for example. This allows the target appliance 10 shown in FIG. 4 to perform control in which the sensibility of the operator is fed back. Therefore, the sensibility feedback control device 100 allows the target appliance 10, which has been uniformly designed regardless of the skill level of the operators, to make an output response corresponding to the operators having various skill levels. Therefore, the sensibility feedback control device 100 can improve the comfort level of the operators having various skill levels.

The weight setting unit including the δ setting unit 50, the control input adjustment unit 70, and the operation input adjustment unit 80 performs weighting corresponding to the operation level of the operator for each of the operation input $v_h(t)$ and the control input $v_c(t)$ to the target appliance 10 by the operator, adds up the weighted operation input $v_h(t)$ and the control input $v_c(t)$, and inputs the resultant to the target appliance 10. Therefore, the weight setting unit can set an appropriate degree of sensibility feedback corresponding to the operation level of the operator. This allows the weight setting unit to increase the degree of sensibility feedback to an unskilled operator, for example, and to reduce the degree of reflection of the operation input of the operator in the target appliance 10. On the contrary, the weight setting unit can reduce the degree of sensibility feedback to a skilled operator and increase the reflection degree of the operation input of the operator in the target appliance 10.

In the sensibility feedback control device 100 of the present embodiment, the sensibility meter 20 may detect three pieces of information of the valence, arousal, and sense of anticipation of the operator as the biometric information $x(t)$, and may determine the sensibility value obtained from the correlation of the three pieces of information as the comfort level $y(t)$. In this case, since the "comfort level", which is sensibility, is quantitatively evaluated, the accuracy of the sensibility feedback control is improved. In this case, regarding the sensibility value obtained from the correlation of the three pieces of information, the three pieces of information and the sensibility value, for example, are calculated by AI-based machine learning.

The sensibility feedback control device 100 of the present embodiment further includes the database 60 in which the target comfort level $r(t)$, the target output $w(t)$, and the comfort level $y(t)$ are sequentially accumulated, and the first control unit 30 may determine the target output $w(t)$ while adjusting the control parameters using the data accumulated in the database 60. In this case, the sensibility feedback control can be performed using the database-driven control without modeling the sensibility of the operator, which is a nonlinear system.

In the sensibility feedback control device 100 of the present embodiment, in a case where the target appliance 10 is a construction machine, the operator can operate the actual construction machine so as to obtain an output $u(t)$ similar to the target output (e.g., target response speed of hydraulic excavator) of the construction machine in the brain.

In the sensibility feedback control device 100 of the present embodiment, the database-driven control of the first control unit 30 may use the learning function. In this case, as the operation time of the target appliance 10 by the operator becomes longer, the target appliance 10 gradually changes so as to make an output response more suitable for the operator. This allows the sensibility feedback control device 100 to further improve the comfort level of the operator.

Example

An example of the sensibility feedback control device 100 will be described below. In the present example, δ is set to "1", and only the control input $v_c(t)$ is input to the target appliance 10. In the present example, database-driven control by the first control unit 30 will be mainly explained.

Figure 5:
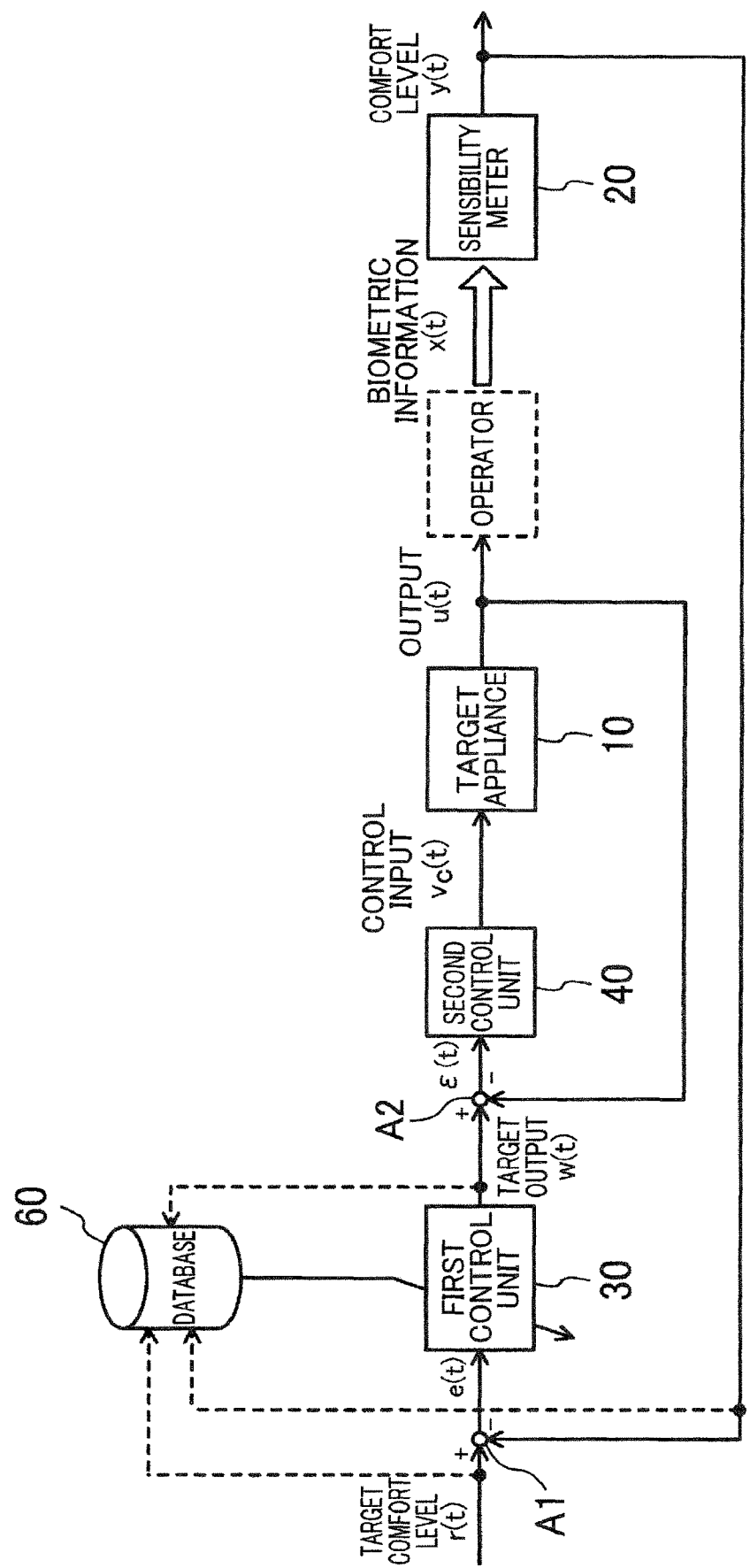
FIG. 5 is a simplified diagram showing a configuration where δ is 1 in the sensibility feedback control device shown in FIG. 1.

FIG. 5 is a diagram showing the configuration in a case where δ is set to 1 in the sensibility feedback control device 100 shown in FIG. 1. Note that in FIG. 5, the same components as those in FIG. 1 are given the same reference numerals. In FIG. 5, the δ setting unit 50, the control input adjustment unit 70, the operation input adjustment unit 80, and the adder A3 are not illustrated.

In the present example, the target appliance 10 is a hydraulic excavator. The output $u(t)$ of the target appliance 10 is the response speed of the bucket of the hydraulic excavator. The control input $v_c(t)$ to the target appliance 10 is torque. The response speed is measured by a sensor, for example. The response speed may be the response speed of another member such as a boom and an arm other than the bucket instead of the response speed of the bucket. That is, the response speed is the response speed of a work device such as the bucket, arm, and boom.

In the present example, the comfort level $y(t)$ of the operator that is the control target is regarded as a nonlinear system, and the database-driven control is applied to the first control unit 30. The second control unit 40 of the inner loop has $K_P'=1.5$, $K_I'=0.1$, $K_D'=0.1$, and performs PID control shown in the expression (2). Therefore, in the present example, the control parameter of the second control unit 40 is not an adjustment target.

In the present example, the comfort level $y(t)$ that is a control target is represented by a discrete-time nonlinear system (hereinafter referred to as a "system") represented by the following expression (3).

[Expression 3]

$$y(t)=f(\phi(t-1)) \qquad (3)$$

In the expression (3), the comfort level $y(t)$ is the output of the system. $f( )$ is a nonlinear function. $\phi(t-1)$ is called an information vector and represents the state prior to time t of the system. The information vector $\phi(t-1)$ is defined by the following expression (4).

[Expression 4]

$$\phi(t-1):=[y(t-1), \ldots, y(t-n_y), w(t-1), \ldots, w(t-n_w)] \qquad (4)$$

Here, the target output $w(t)$ is an input of the system with respect to control of the comfort level $y(t)$. $n_y$ is the order of output of the system. $n_w$ is the order of input of the system. In database-driven control, each operation data is accumulated in the database 60 (see FIG. 3) in the form of the expression (4). $\phi(t)$ is an information vector representing the current state of the system, and is called a request point (query).

As the control law of the first control unit 30, a speed type I-PD control law represented by the following expression (5) is used.

[Expression 5]

$$\phi w(t)=K_I(t)e(t)-K_P(t)\Delta y(t)-K_D(t)\Delta^2 y(t) \qquad (5)$$

In the expression (5), $e(t)$ is a control error signal. $e(t)$ is defined by the following expression (6) where $r(t)$ is the target comfort level.

[Expression 6]

$$e(t):=r(t)-y(t) \qquad (6)$$

In the expression (5), $K_P(t)$, $K_I(t)$, and $K_D(t)$ are proportional gain, integral gain, and differential gain, respectively, in each step (time t). Furthermore, $\Delta(:=1-z^{-1})$ is a difference operator. $z^{-1}$ is a delay operator.

Figure 6:
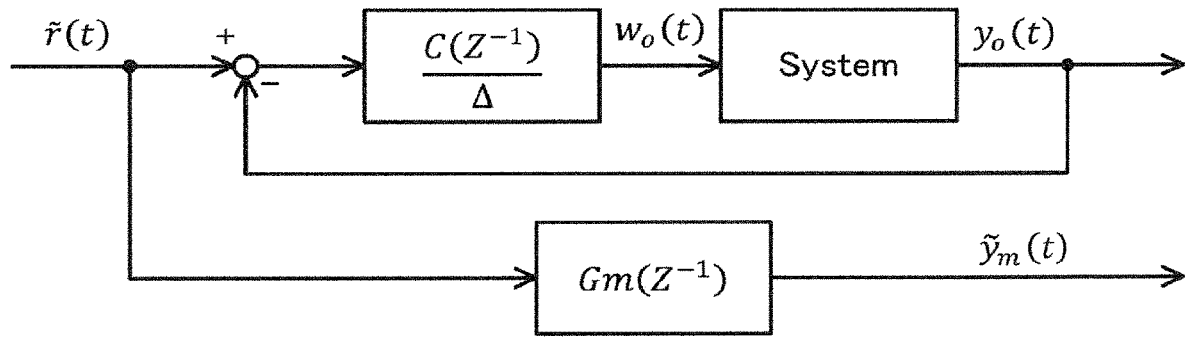
FIG. 6 is a block diagram of the FRIT used in the sensibility feedback control device according to the embodiment.

In the present example, the first control unit 30 directly calculates the control parameter of the first control unit 30 using the input/output data $w_0(t)$ and $y_0(t)$ obtained by one operation experiment using the FRIT method and the pseudo reference input $\sim r(t)$ generated from these experiment data. FIG. 6 is a block diagram of the FRIT used in the present example. In FIG. 6, System is the second control unit 40, the target appliance 10, and the sensibility meter 20. $C(z^{-1})$ is a controller. The controller can be represented by the following expression (7).

[Expression 7]

$$C(z^{-1}) = c_0 + c_1 z^{-1} + \ldots + c_n z^{-n} \quad (7)$$

In the expression (7), n is the order of the control law. In the case of PID control law, n=2. As shown in FIG. 6, the input/output relationship of $C(z^{-1})$ is expressed by the following expression (8).

[Expression 8]

$$w_0(t) = \frac{C(z^{-1})}{\Delta}\{\tilde{r}(t) - y_0(t)\} \quad (8)$$

From the expression (8), the pseudo reference input ~r is calculated as the expression (9) below.

[Expression 9]

$$\tilde{r}(t) = C^{-1}(z^{-1})\Delta w_0(t) + y_0(t) \quad (9)$$

In the FRIT method, as shown in FIG. 6, a reference model $G_m(z^{-1})$ having a desired characteristic designed in advance is used. Based on the output $\sim y_m(t)$ of the reference model $G_m(z^{-1})$ with respect to the pseudo reference input $\sim r$, the first control unit 30 calculates the control parameter so that the error between the output $\sim y_m(t)$ and $y_0(t)$ becomes small. The reference model $G_m(z^{-1})$ is represented by a characteristic polynomial of the following expressions (10) and (11).

[Expression 10]

$$G_m(z^{-1}) := 1 + p_1 z^{-1} + p_2 z^{-2} \quad (10)$$

[Expression 11]

$$\left.\begin{array}{l} p_1 = -2\exp\left(-\frac{\rho}{\mu}\right)\cos\left(\frac{\sqrt{4\mu - 1}}{2\mu}\rho\right) \\ p_2 = \exp\left(-\frac{\rho}{\mu}\right) \\ \rho := T_s/\sigma \\ \mu := 0.25(1-\alpha) + 0.51\alpha \end{array}\right\} \quad (11)$$

In the expression (11), α represents the rising characteristic of the control system. σ represents a parameter relevant to the damping characteristic. Each of α and σ can be optionally set. $T_s$ is the sampling time. Specifically, σ is the time until the output of the control system reaches about 60% of the step-like target value. It is desirable that α is set in a range of 0 or more and 2.0 or less. α=0 indicates the response of the Binomial model. α=1 indicates the response of the Butterworth model.

The design procedure of the database-driven PID control device will be described below.

<Creation of Initial Database>

In database-driven control, if past accumulation data do not exist, the design of a local controller cannot be performed in principle. Therefore, in the present example, from the input/output data obtained around a certain equilibrium point, Zieglar & Nichols (ZN) method, Chien, Hrones & Reswick (CHR) method, or the like is used to calculate the PID gain (control parameter), and an initial database including an information vector (represented by the following expression (12)) made up of the PID gain and the above-described input/output data is created. The ZN method is disclosed in the literature "J. G. Zieglar et al., Optimum settings for automatic controllers, Trans. ASME, Vol. 64, No. 8, pp. 759-768 (1942)". The CHR method is disclosed in the literature "K. L. Chien et al., On the Automatic Control of Generalized Passive Systems, Trans. ASME, Vol. 74, pp. 175-185 (1972)". The input/output data obtained around the equilibrium point is, for example, a set of data having the same characteristics.

[Expression 12]

$$\phi_i(j) := [\bar{\phi}(j), K(j)] \quad (12)$$

In the expression (12), j=1, 2, . . . , N(0), i=1, 2, . . . M, and $\bar{\phi}(j)$ and K(j) are given by the following expressions (13) and (14), respectively.

[Expression 13]

$$\bar{\phi}(t) := [r(t+1), r(t), y(t) \ldots, y(t-n_y+1), w(t-1), \ldots, w(t-n_w+1)] \quad (13)$$

[Expression 14]

$$K(t) := [K_P(t), K_I(t), K_D(t)] \quad (14)$$

N(0) is the number of initial data (number of information vectors in the initial database). M is the number of elements. Since the PID gain in the initial database is fixed, K(1)=K(2)= . . . =K(N(0)).

The processing of creating the initial database above is executed when the system is not in operation by using the operation data accumulated in the database 60 while the system is in operation.

<Calculation of Distance and Selection of Neighborhood>

The distance between the request point $\phi(t)$ and the information vector $\bar{\phi}(j)$ accumulated in the database is obtained by a weighted Li norm represented by the following expression (15).

[Expression 15]

$$d(\bar{\phi}(t), \bar{\phi}(j)) = \sum_{l=1}^{n_y+n_w+1} \left| \frac{\bar{\phi}_l(t) - \bar{\phi}_l(j)}{\max \bar{\phi}_l(m) - \min \bar{\phi}_l(m)} \right| \quad (15)$$

(where $j = 1, 2, \ldots, N(t)$)

N(t) is the number of data (number of information vectors) accumulated in the database at time t. $\bar{\phi}_l(j)$ is the lth element of the jth information vector. $\bar{\phi}_l(t)$ is the lth element of the request point at time t. $\max \bar{\phi}_l(m)$ is the largest element of the lth element of all the information vectors ($\bar{\phi}(j)$: j=1, 2, . . . , N(t)) present in the database. $\min \bar{\phi}_l(m)$ is the smallest element of the lth elements.

In the present example, k information vectors are selected from the database in ascending order of the distance d shown in the expression (15), and the selected data set is defined as neighborhood data.

<Configuration of Local Controller>

Next, in the present example, the linearly weighted average (LWA) represented by the following expression (16) is applied to the neighborhood data selected as described above, and a local controller is configured.

[Expression 16]

$$K(t) = \sum_{i=1}^{k} w_i K(i), \quad \sum_{i=1}^{k} w_i = 1 \qquad (16)$$

Here, $w_i$ is a weight with respect to K(i) included in the ith information vector of the neighborhood data, and is given by the following expression (17).

[Expression 17]

$$w_i = \sum_{l=1}^{n_y+n_w+1} \left(1 - \frac{[\bar{\phi}_l(t) - \bar{\phi}_l(i)]^2}{[\max \bar{\phi}_l(m) - \min \bar{\phi}_l(m)]^2}\right) \qquad (17)$$

The PID gain at each time t is calculated by the above procedure. Furthermore, in order to enable the database-driven control system to appropriately adjust the PID gain at each equilibrium point, it is necessary to perform learning of database (update of control parameters). Therefore, in the present example, FRIT is applied, and the PID gain in each data set in the database is updated offline by learning from the initial data used to construct the database. The offline is a state before the system is operated, for example, when the target appliance 10 is not in operation.

<Offline Learning of Database-Driven Control Using FRIT>

The offline learning of the database-driven control using FRIT will be specifically described below. First, in order to calculate the PID gain at the request point $\bar{\phi}_0(t)$ in closed loop data, the distance between the request point and the information vector in the database 60 is calculated by the expression (15), and k neighborhood data are selected from the calculation result. Subsequently, the PID gain is calculated by the expression (16). The steepest descent method represented by the following expressions (18) and (19) is applied to the calculated PID gain. Thus, the PID gain $K^{old}(t)$ is learned, and a new PID gain $K^{new}$ is derived.

[Expression 18]

$$K^{new}(t) = K^{old}(t) - \eta \frac{\partial J(t+1)}{\partial K(i)} \qquad (18)$$

[Expression 19]

$$\eta := [\eta_P, \eta_I, \eta_D] \qquad (19)$$

In the expressions (18) and (19), is a learning coefficient, and J(t+1) is an evaluation norm defined by the following expressions (20) and (21).

[Expression 20]

$$J(t+1) := \frac{1}{2}\varepsilon(t+1)^2 \qquad (20)$$

[Expression 21]

$$\varepsilon(t) := y_0(t) - \tilde{y}_m(t) \qquad (21)$$

where $\sim y_m(t)$ is designed as the following expression (22).

[Expression 22]

$$\tilde{y}_m(t) = \frac{z^{-1} G_m(1)}{G_m(z^{-1})} \tilde{r}(t) \qquad (22)$$

In the expression (22), $G_m(1)=1+p_1+p_2$ (see expression (10)).

The partial differential of each of the right side second term of the expression (18) is expanded as in the expression (23).

[Expression 23]

$$\begin{aligned}
\frac{\partial J(t+1)}{\partial K_P(t)} &= \frac{\partial J(t+1)}{\partial \tilde{y}_m(t+1)} \frac{\partial \tilde{y}_m(t+1)}{\partial \tilde{r}(t)} \frac{\partial \tilde{r}(t)}{\partial K_P(t)} \\
&= -\frac{\varepsilon(t+1) G_m(1) \Delta y_0(t)}{K_I^{old}(t)} \\
\frac{\partial J(t+1)}{\partial K_I(t)} &= \frac{\partial J(t+1)}{\partial \tilde{y}_m(t+1)} \frac{\partial \tilde{y}_m(t+1)}{\partial \tilde{r}(t)} \frac{\partial \tilde{r}(t)}{\partial K_I(t)} \\
&= -\frac{\varepsilon(t+1) G_m(1) \Gamma(t)}{K_I^{old}(t)^2} \\
\frac{\partial J(t+1)}{\partial K_D(t)} &= \frac{\partial J(t+1)}{\partial \tilde{y}_m(t+1)} \frac{\partial \tilde{y}_m(t+1)}{\partial \tilde{r}(t)} \frac{\partial \tilde{r}(t)}{\partial K_D(t)} \\
&= -\frac{\varepsilon(t+1) G_m(1) \Delta^2 y_0(t)}{K_I^{old}(t)}
\end{aligned} \qquad (23)$$

In the expression (23), $\Gamma(t)$ is represented as in the following expression (24).

[Expression 24]

$$\Gamma(t) = -\Delta u_0(t) - K_P^{old}(t) + K_D^{old}(t) y_0(t) + \qquad (24)$$
$$\{K_P^{old}(t) + 2K_D^{old}(t)\} y_0(t-1) - $$
$$K_D^{old}(t) y_0(t-2)$$

Since the expression (23) includes the pseudo reference input ~r(t), the expression (18) is of FRIT-based offline learning. Each neighborhood data on the database is updated by using $K^{new}(t)$ obtained by the expression (18). This procedure is repeated until the evaluation norm expressed by the expression (20) becomes sufficiently small. Due to this, an optimum database is acquired. When the database-driven control is applied to the system, the local controller is configured at each step (time) in accordance with the procedure explained in the above-described sections of "Creation of initial database", "Calculation of distance and selection of neighborhood", and "Configuration of local controller". This achieves a more effective control performance for the nonlinear system.

<Online Learning of Database-Driven Control Using FRIT>

The PID gain obtained by the offline learning described above is further updated by the following online learning. Online learning is done when the system is online. Online means that the system is in operation.

In the online learning, the gradient descent method shown in the expressions (25) and (26) is applied to the PID gains obtained by offline learning.

[Expression 25]

$$K^{new}(t) = K^{old}(t) - \eta \frac{\partial J(t+1)}{\partial K(i)} \quad (25)$$

[Expression 26]

$$\eta := [\eta_P, \eta_I, \eta_D] \quad (26)$$

In the expressions (25) and (26), η is a learning coefficient, and J(t+1) is an evaluation norm defined by the following expressions (27) and (28). The difference from offline learning is that $y_0(t)$ expressed in the expression (21) is y(t) in the expression (28).

$y_m(t)$ is represented by the expression (29).

[Expression 27]

$$J(t+1) := \frac{1}{2}\varepsilon(t+1)^2 \quad (27)$$

[Expression 28]

$$\varepsilon(t) := y_m(t) - y(t) \quad (28)$$

[Expression 29]

$$y_m(t) = \frac{z^{-1} G_m(1)}{G_m(z^{-1})} r(t) \quad (29)$$

$G_m(z^{-1})$ is a characteristic polynomial of the reference model and is represented by the expressions (30) and (31).

[Expression 30]

$$G_m(z^{-1}) := 1 + p_1 z^{-1} + p_2 z^{-2} \quad (30)$$

[Expression 31]

$$\begin{aligned}
p_1 &= -2\exp\left(-\frac{\rho}{\mu}\right)\cos\left(\frac{\sqrt{4\mu-1}}{2\mu}\rho\right) \\
p_2 &= \exp\left(-\frac{\rho}{\mu}\right) \\
\rho &:= T_s/\sigma \\
\mu &:= 0.25(1-\delta) + 0.51\delta
\end{aligned} \quad (31)$$

δ is the rise characteristic of the control system. σ is a parameter regarding the damping characteristics. Each of δ and σ is optionally set by the designer. The partial differential of the right side second term of the expression (25) is expressed by the expression (32).

[Expression 32]

$$\begin{aligned}
\frac{\partial J(t+1)}{\partial K_P(t)} &= \frac{\partial J(t+1)}{\partial \varepsilon(t+1)} \frac{\partial \varepsilon(t+1)}{\partial y(t+1)} \frac{\partial y(t+1)}{\partial w(t)} \frac{\partial w(t)}{\partial K_P(t)} \\
&= \varepsilon(t+1)\Delta y(t) \frac{\partial y(t+1)}{\partial w(t)} \\
\frac{\partial J(t+1)}{\partial K_I(t)} &= \frac{\partial J(t+1)}{\partial \varepsilon(t+1)} \frac{\partial \varepsilon(t+1)}{\partial y(t+1)} \frac{\partial y(t+1)}{\partial w(t)} \frac{\partial w(t)}{\partial K_I(t)} \\
&= -\varepsilon(t+1)e(t)\frac{\partial y(t+1)}{\partial w(t)} \\
\frac{\partial J(t+1)}{\partial K_D(t)} &= \frac{\partial J(t+1)}{\partial \varepsilon(t+1)} \frac{\partial \varepsilon(t+1)}{\partial y(t+1)} \frac{\partial y(t+1)}{\partial w(t)} \frac{\partial w(t)}{\partial K_D(t)} \\
&= \varepsilon(t+1)\Delta^2 y(t)\frac{\partial y(t+1)}{\partial w(t)}
\end{aligned} \quad (32)$$

The PID gain calculated by online learning is applied as a control parameter of the expression (1).

Numerical Example

A numerical example of the sensibility feedback control according to the present example will be described below.

Here, it is assumed that the target appliance (appliance operated by the operator) 10 shown in FIG. 5 is a hydraulic excavator. In this case, the target appliance 10 is represented by the first-order delay system of the following expression (33).

[Expression 33]

$$G_2(s) = \frac{100}{1 + 100s} \quad (33)$$

On the other hand, the comfort level y(t) is expressed by using the Weber-Fechner laws (See "I. P. Herman, Physics of the Human Body: Biological and Medical Physics, Biomedical Engineering, Springer-Verlag GmbH & CO. KG (2007)") presented in the following expressions (34) and (35). In the expressions (34) and (35), the comfort level y(t) has the maximum value of 1.

[Expression 34]

$$y(t) = \frac{1}{1 + E(t) \cdot \log(1 + e_h(t))} \quad (34)$$

[Expression 35]

$$e_h(t) = w_h(t) - u(t) \quad (35)$$

In the expressions (34) and (35), $w_h(t)$ is the target speed of the hydraulic excavator that the operator has in the brain, but this is unknown to the control system. $e_h(t)$ is the speed error of the hydraulic excavator felt in the operator's brain.

Figure 7:
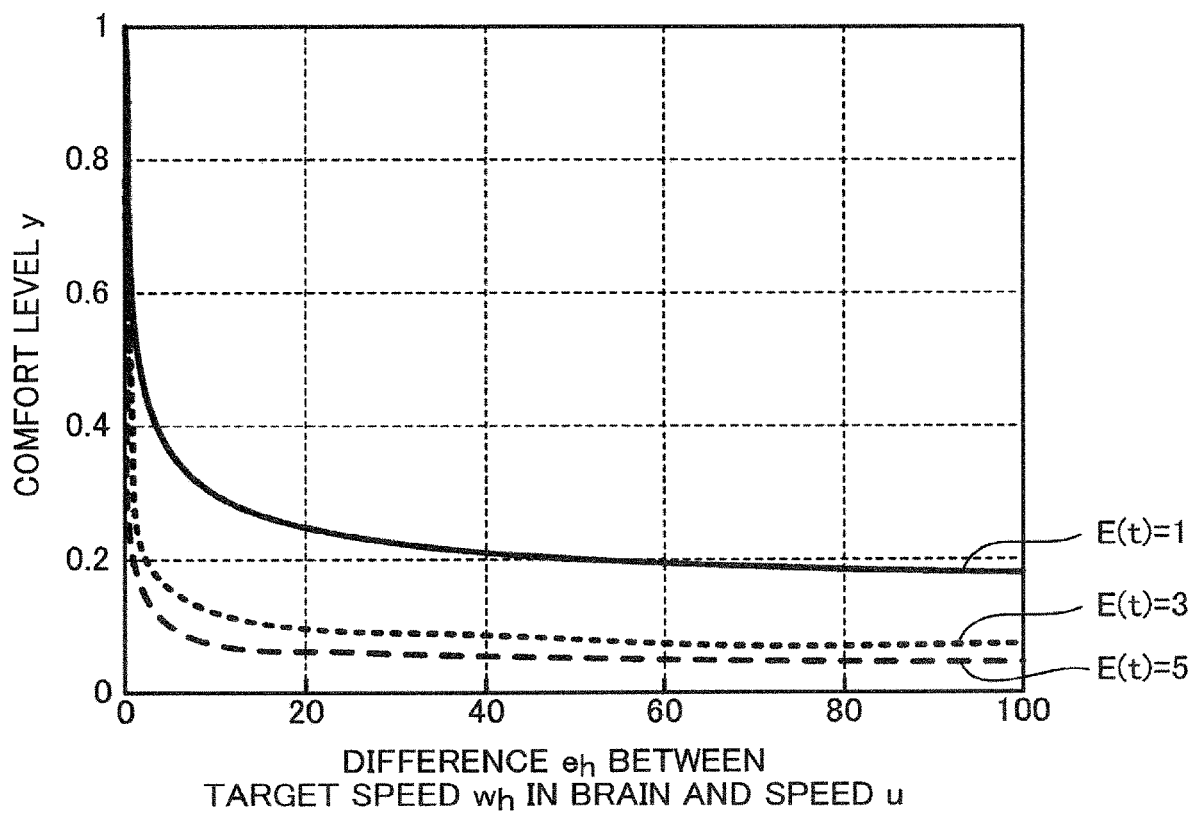
FIG. 7 is a graph showing the relationship between a speed error $e_h(t)$ in the brain of the operator and a comfort level y(t).

From the expression (34), if the speed error $e_h(t)$ in the brain of the operator is completely zero, the comfort level y(t) becomes 1, which is the maximum. E(t) is a variable relating to the comfort level y(t) and has a different value depending on the operator. FIG. 7 is a graph showing the relationship between the speed error $e_h(t)$ in the brain of the operator and the comfort level y(t). As shown in FIG. 7, as the speed error $e_h(t)$ becomes larger, the comfort level y(t) further decreases. As E(t) becomes larger, the rate of decrease in the comfort level y(t) becomes larger.

The setting parameters in the numerical example described below were r=0.8, $w_h$=40, σ=10, α=0, η=[80, 60, 80].

Existing control parameters were used for the second control unit 40 of the inner loop. For adjustment of the control parameters of the first control unit 30 of the outer loop, database-driven control (see "Wakitani Shin, et al., Design of FRIT-Based Nonlinear PID Control Systems, Journal of the Society of Instrument and Control Engineers, Vol. 52, No. 10, pp. 885-891 (2013)") effective for the nonlinear system was used.

The PID gains of the outer loop (first control unit 30) for acquiring the initial data $\{u_0, y_0\}$ were $K_P$=3.5, $K_I$=0.5, $K_D$=3.5. The PID gains of the inner loop (second control unit 40) were $K_P'$=1.5, $K_I'$=0.1, $K_D'$=0.1.

The sensibility feedback control was performed while adjusting the control parameters of the first control unit 30 by the database-driven control in the above setting. FIG. 8 shows graphs showing the comfort level y(t), the output u(t) (speed), and the control input $v_c(t)$ (torque) in each step (time) in the present numerical example. FIG. 9 shows graphs showing adjusted control parameters (PID gain) at each step (time).

As represented by the expression (34), the comfort level y(t) is a nonlinear system. Therefore, as shown in the upper graph of FIG. 8, the initial data $y_0$ obtained in the state where the PID gain is fixed does not follow the target comfort level r(=0.8). In the present example, on the other hand, the PID gain is adjusted by the database-driven control. Therefore, as shown in the upper graph of FIG. 8, the comfort level y follows the target comfort level r. This indicates that the sensibility feedback control has been achieved in the present example. This is because the PID gain is adaptively adjusted as shown in FIG. 9.

While the target output $w_h$ (=40: target speed) in the brain of the operator is unknown to the control system, the target output w (target speed) obtained by the present example finally becomes 40 (middle graph of FIG. 8). This allows the target speed in the brain of the operator to be estimated by analyzing the database.

As shown in the lower graph of FIG. 8, it is indicated that when the load is large, a large control input $v_c(t)$ (torque) is automatically calculated accordingly.

Comparative Example

A comparative example of the sensibility feedback control of the present embodiment will be described below. In this comparative example, the sensibility feedback control is achieved only by an outer loop. That is, in this comparative example, the inner control loop relating to the target appliance is omitted. Hereinafter, the effectiveness of the cascade control system (outer loop+inner loop) in the sensibility feedback control of the present embodiment will be described using this comparative example.

Figure 10:
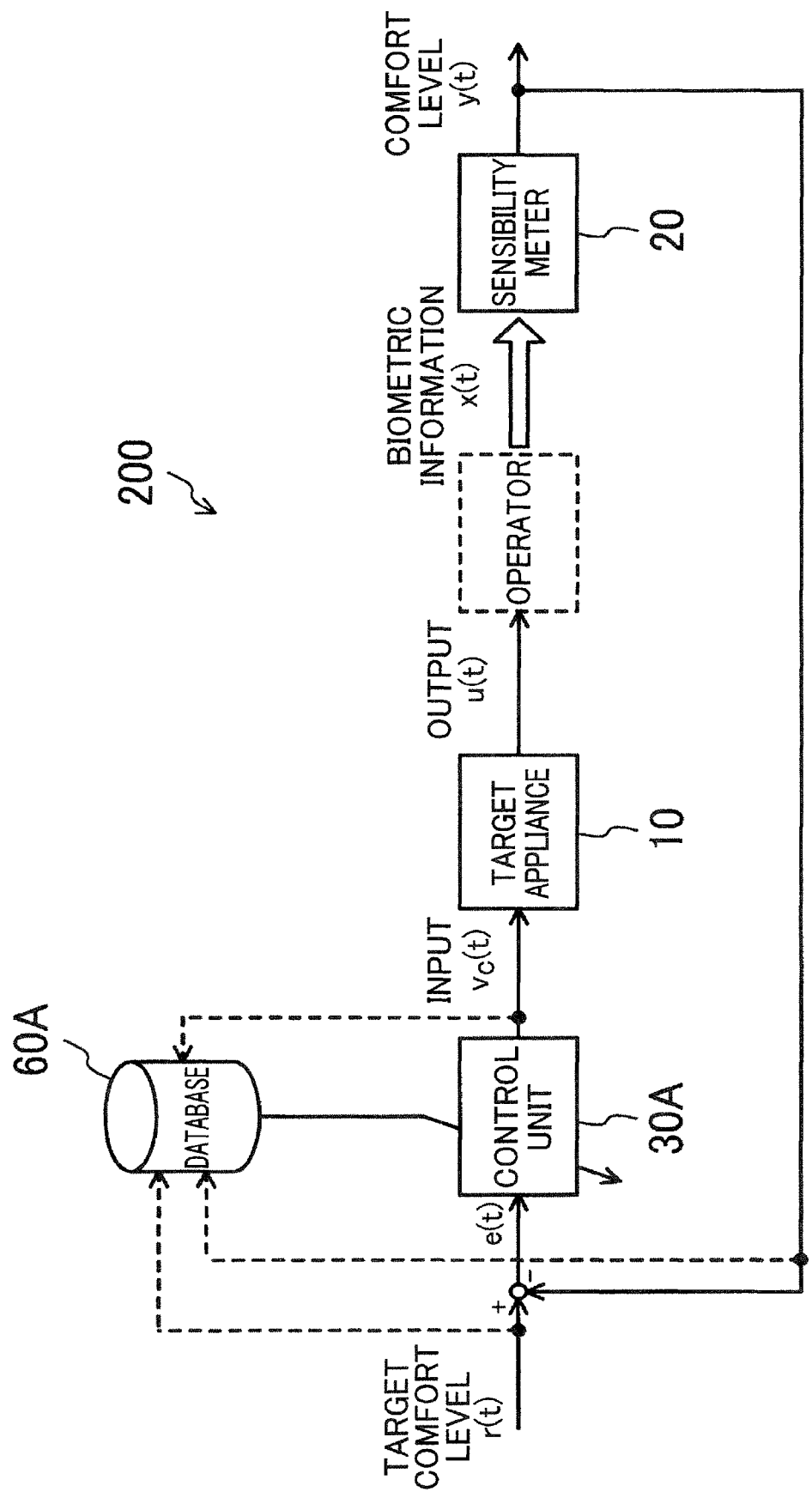
FIG. 10 is a configuration diagram of the sensibility feedback control device according to a comparative example.

FIG. 10 is a configuration diagram of the sensibility feedback control device according to the comparative example. As shown in FIG. 10, a sensibility feedback control device 200 according to the comparative example includes the target appliance 10, the sensibility meter 20, a control unit 30A, and a database 60A. The target appliance 10 is a hydraulic excavator operated by an operator as in the above-described example. The sensibility meter 20 is similar to the sensibility meter 20 of the sensibility feedback control device 200 of the present embodiment shown in FIG. 1. The sensibility meter 20 detects biometric information x(t) relating to the operator corresponding to an output u(t) from the target appliance 10, and determines a comfort level y(t) of the operator based on the biometric information x(t). The control unit 30A determines the control input $v_c(t)$ to the target appliance 10 based on the difference e(t) between the target value (target comfort level) r(t) relating to the comfort level y(t) and the comfort level y(t).

The control unit 30A executes PID control represented by the following expression (36) using, for example, $K_P''$, $K_I''$, and $K_D''$ as PID gains.

[Expression 36]

$$v_c(t) = K_P'' e(t) + K_I'' \int_0^t e(\tau)d\tau + K_D'' \frac{de(t)}{dt} \quad (36)$$

The control unit 30A performs database-driven control using the database 60A. In the database 60A, data necessary for adjustment of the PID gain of the control unit 30A, for example, the target comfort level r(t), the comfort level y(t), the control input $v_c(t)$, and the like are sequentially accumulated.

Also in this comparative example, the output u(t) of the target appliance 10 is the response speed of the bucket of the hydraulic excavator, and the control input $v_c(t)$ to the target appliance 10 is torque.

FIG. 11 shows graphs showing a result of performing sensibility feedback control while performing adjustment of the control parameter of the control unit 30A by the database-driven control in the comparative example. In FIG. 11, the upper graph presents the comfort level y(t) at each step (time). The middle graph presents the output u(t) (speed) at each step (time). The lower graph presents the control input $v_c(t)$ (torque) at each step (time). The PID gains of the control unit 30A for acquiring the initial data $\{u_0, y_0\}$ were $K_P$=3.5, $K_I$=0.5, $K_D$=3.5, as in the above-described example. The other parameters were also r=0.8, $w_h$=40, σ=10, α=0, η=[80, 60, 80] as in the above-described example.

As shown in the upper graph of FIG. 11, in the comparative example, the PID gain is adjusted by the database-driven control, but the comfort level y does not follow the target comfort level r. That is, the sensibility feedback control according to the comparative example cannot achieve sufficient control performance.

From this result, in the sensibility feedback control of the present embodiment, the responsiveness of the inner loop (second control unit 40) is improved by the cascade control system. Thus, in the present embodiment, the design of the control system becomes easy, and the accuracy of the sensibility feedback control can be improved.

While the embodiments (including examples) of the present invention have been described above, the present invention is not limited to the above-described embodiments, and various modifications can be made within the scope of the invention. That is, the description of the above-described embodiments is essentially illustrative only and is not intended to limit the invention, its application, or its use.

For example, in the present embodiment, the sensibility feedback control device has been described with an example of a hydraulic excavator (construction machine), but it is similarly applicable also to other appliances operated by an operator.

The invention claimed is:

1. A sensibility feedback control device comprising:
a target appliance to be operated by an operator;
a sensibility meter configured to detect biometric information relating to the operator corresponding to an output from the target appliance, and determines a comfort level of the operator based on the biometric information;
first control circuitry configured to determine a second target value relating to the output based on a difference between a first target value relating to the comfort level and the comfort level;
second control circuitry configured to determine a control input to the target appliance based on a difference between the second target value and the output;
weight setting circuitry configured to perform weighting corresponding to an operation level of the operator, for an operation input to the target appliance by the operator, and for the control input; and an adder configured to add the operation input and the control input, each of which has been weighted by the weight setting circuitry, and input an obtained value to the target appliance.

2. The sensibility feedback control device according to claim 1, wherein
the sensibility meter is configured to detect three pieces of information of valence, arousal, and sense of anticipation of the operator as the biometric information, and determines a sensibility value obtained from correlation of the three pieces of information as the comfort level.

3. The sensibility feedback control device according to claim 1, further comprising a database in which the first target value, the second target value, and the comfort level are sequentially accumulated,
wherein the first control circuitry is configured to determine the second target value while adjusting a control parameter using data accumulated in the database.

4. The sensibility feedback control device according to claim 3, wherein the control parameters are proportional gain, integral gain, and differential gain.

5. The sensibility feedback control device according to claim 1, wherein the target appliance is a construction machine.

6. The sensibility feedback control device according to claim 5, wherein the output is a response speed of a work device included in the construction machine.

* * * * *